(12) United States Patent
Duckett, III

(10) Patent No.: US 10,806,332 B2
(45) Date of Patent: Oct. 20, 2020

(54) FLUORESCENCE IMAGING SCOPE WITH REDUCED CHROMATIC ABERRATION

(71) Applicant: KARL STORZ Imaging, Inc., Goleta, CA (US)

(72) Inventor: George E. Duckett, III, Castaic, CA (US)

(73) Assignee: KARL STORZ Imaging, Inc., Goleta, CA (US)

(*) Notice: Subject to any disclaimer, the term of this patent is extended or adjusted under 35 U.S.C. 154(b) by 283 days.

(21) Appl. No.: 15/790,941

(22) Filed: Oct. 23, 2017

(65) Prior Publication Data

US 2019/0117051 A1   Apr. 25, 2019

(51) Int. Cl.

| | | |
|---|---|---|
| *A61B 5/00* | (2006.01) | |
| *A61B 1/055* | (2006.01) | |
| *G02B 23/24* | (2006.01) | |
| *A61B 1/06* | (2006.01) | |
| *A61B 1/04* | (2006.01) | |

(Continued)

(52) U.S. Cl.
CPC ............. *A61B 1/043* (2013.01); *A61B 1/002* (2013.01); *A61B 1/0019* (2013.01); *A61B 1/00096* (2013.01); *A61B 1/053* (2013.01); *A61B 1/055* (2013.01); *A61B 1/0638* (2013.01); *A61B 1/0653* (2013.01); *A61B 5/0035* (2013.01); *A61B 5/0071* (2013.01); *A61B 5/0086* (2013.01); *G02B 21/0032* (2013.01); *G02B 21/0064* (2013.01); *G02B 23/2453* (2013.01)

(58) Field of Classification Search
None
See application file for complete search history.

(56) References Cited

U.S. PATENT DOCUMENTS

| | | | | |
|---|---|---|---|---|
| 5,020,893 A | * | 6/1991 | Karst | ................ G02B 23/2446 359/435 |
| 5,910,816 A | | 6/1999 | Fontenot | |

(Continued)

OTHER PUBLICATIONS

J. T. Alander, I. Kaartinen, A. Laakso, T. Patila, T. Spillmann, V. V. Tuchin, M. Venermo, P. Valisuo "A review of indocyanine green fluorescent imaging in surgery," Int. J. of Biomedical Imaging, 2012, pp. 1-26, Hindawi Publishing Corp., United Kingdom.

*Primary Examiner* — John P Leubecker
*Assistant Examiner* — Minqiao Huang
(74) *Attorney, Agent, or Firm* — Michael Joseph Loi; David Noel Villalpando

(57) ABSTRACT

Improved fluoresced imaging (FI) endoscope devices and systems are provided to enhance use of endoscopes with FI and visible light capabilities. An endoscope device is provided for endoscopy imaging in a white light and a fluoresced light mode. A chromatic adjustment assembly, typically implemented with prisms, compensates for a chromatic focal difference between the white light image and the fluoresced light image caused by the dispersive properties of the optical materials or optical design employed in the construction of the optical channel. The assembly is placed optically between the most proximal rod lens of the endoscope and the focusing optics, typically at an internal telecentric image space, to improve the chromatic correction. The prism assembly directs incoming light with different spectral content along separate paths which compensate for chromatic aberration.

6 Claims, 7 Drawing Sheets

(51) Int. Cl.
  *A61B 1/002*    (2006.01)
  *A61B 1/00*     (2006.01)
  *A61B 1/05*     (2006.01)
  *G02B 21/00*    (2006.01)

(56) References Cited

U.S. PATENT DOCUMENTS

| | | |
|---|---|---|
| 8,295,693 B2 | 10/2012 | McDowall |
| 8,437,629 B2 | 5/2013 | McDowall |
| 8,773,756 B2 * | 7/2014 | Tesar .................. G01J 3/36 359/353 |
| 2014/0378769 A1 | 12/2014 | Rehe |
| 2015/0256721 A1 | 9/2015 | Moore |

* cited by examiner

FLUORESCENCE IMAGING SCOPE WITH REDUCED CHROMATIC ABERRATION

TECHNICAL FIELD OF THE INVENTION

The invention relates generally to the field of medical image capture and more specifically to endoscope designs for improving performance fluorescent imaging and visible color imaging.

BACKGROUND OF THE INVENTION

Endoscopes and other medical scopes often use fluorescing agents or autofluorescence to better examine tissue. A fluorescing agent such as a dye may be injected or otherwise administered to tissue, and then an excitation light is directed toward the tissue. Responsive to the excitation light, the fluorescing agent fluoresces (emits light typically at a longer wavelength than the excitation light), allowing a sensor to detect the light, which is often not in a wavelength visible to the human eye. The detected light is formatted to images, and examining the images can indicate the concentration of fluorescing agent in the observed tissue. Further, a phenomenon known as autofluorescence may occur in which tissue fluoresces light under certain conditions without a fluorescing agent. Such light can be detected as well. Images based on detected fluoresced light, known as "fluorescence imaging" (FI), are therefore useful in medical diagnosis, testing, and many scientific fields.

A typical prior art endoscope 2, as illustrated in FIG. 1, usually includes a first imaging lens (e.g., an objective) followed by a series of carrier lenses (e.g., relays) which capture and transmit an optical image from inside an enclosed area 1 to the outside. The proximal end of the endoscope 2 may be attached, via direct coupling or an adaptor, to a camera head 3 or an eye-piece for viewing. The camera head 3 usually includes lenses for receiving the optical image and forming a real optical image onto the image sensor. The digital image captured by the image sensor can then be transmitted to a camera control unit (CCU) or other similar modules for analysis and display.

Frequently, endoscopes used for FI applications, and particularly indocyanine green (ICG) applications are mainly designed and deployed for visible light imagery. As such, they are not typically designed to maintain a constant focus between infrared light and visible light. To perform FI imaging, such scopes often employ an appropriate optical filter to block the stimulus light and transmit the fluoresced light. Since these endoscopes are designed for use with visible light, the infrared fluorescence is focused in a different plane than the visible light. There are existing efforts to compensate for the focal difference. Some endoscopic camera heads employ multiple sensors, with sensors in different focal planes. The various spectral bands are detected on the multiple sensors, each an individually appropriate focal plane. This approach is disadvantageous not only due to the complexity and cost of using multiple image sensors, but also in that various models of endoscopes will have varying amounts of chromatic error, requiring many configurations of camera head designs.

It is very difficult to construct a single camera head capable of compensating for a variety of endoscope models. Other efforts to compensate for focal differences, such as, for example, that found in U.S. Pat. No. 8,773,756 to Tesar, et al., involve using an optical coupler that splits the light into two paths, a visible spectrum path and a NIR spectrum path. Different lenses or prisms are used in each path to compensate for the chromatic differences. However, such systems still fail to compensate for the variety of chromatic aberrations across the desired spectrum, or to compensate for differences between various endoscopes. There is also chromatic aberration in the deep blue range of the visible spectrum. The dispersive properties of the optical materials used in endoscopes, and long glass paths through such optical materials, make conventional correction of the entire spectrum from deep blue to infrared particularly difficult. Finally, the chromatic aberration includes both longitudinal chromatic aberration and lateral chromatic aberration due to obliquely incident light from the object space. Techniques that using lenses or prisms to correct for longitudinal chromatic aberration often introduce unwanted lateral chromatic aberration.

What is needed are devices and methods to enable an endoscopic camera to compensate for the endoscope characteristics to improve correction of the entire spectrum from deep blue to infrared. What is further needed are devices allowing the use of varied existing endoscopes for fluorescence imaging applications without expensive and slow optical elements such as autofocus mechanisms or lenses and processing systems for chromatic aberration correction.

SUMMARY OF THE INVENTION

It is an object of the invention to improve correction of the entire spectrum from deep blue to infrared. In order to achieve these objects, various aspects of the invention provide improved fluoresced imaging (FI) endoscope devices and systems are provided to enhance use of endoscopes with FI and visible light capabilities. An endoscope device is provided for endoscopy imaging in a white light and a fluoresced light mode. A chromatic adjustment assembly, typically implemented with prisms, compensates for a chromatic focal difference between the white light image and the fluoresced light image caused by the dispersive properties of the optical materials or optical design employed in the construction of the optical channel. The assembly is placed optically between the most proximal rod lens of the endoscope and the focusing optics, typically at an internal telecentric image space to improve the chromatic correction. The prism assembly directs incoming light with different spectral content along separate paths which compensate for chromatic aberration.

According to a first aspect of the invention, an optical device is provided for use in endoscope procedures, the device operable with white light and fluoresced light outside the visible band. The device has an elongated shaft having multiple lenses including an objective lens group forming an image at the distal end and multiple rod lenses which relay the image formed at the distal end to the proximal end. A beamsplitter and prism assembly is optically positioned proximal to the most proximal rod lens and distal to a second lens group and comprising a first beamsplitter adapted to direct a first portion of light with a first spectral content along a first optical path and a second portion of light with a second spectral content, different from the first, along a second optical path. A second beamsplitter is optically arranged proximal to the beamsplitter and prism assembly and distal to the second lens group and adapted to recombine the first portion of light and the second portion of light to a common optical axis. The first optical path and the second optical path are adapted to compensate for chromatic aberration of the endoscope multiple lenses such that the first portion of light and the second portion of light are focused onto substantially the same image plane.

According to some implementations of the first aspect, the first portion of light contains both visible and infrared spectral content. In some versions the second portion of light also contains both visible and infrared spectral content. In such case, the visible content of the second portion of light may be of longer wavelength than the visible content of the first portion of light, with the infrared content of the second portion of light having shorter wavelength than the infrared portion of the first portion of light. In such case, the first portion of light may include light with wavelengths less than approximately 450 nm and longer than approximately 750 nm, and the second portion of light include light with wavelengths between approximately 450 nm and 750 nm. By utilizing a beam splitter and prism assembly, part of the infrared and the deep blue wavelengths can propagate along one optical path while the rest of the visible light and some infrared propagate along a separate path having a different optical path length. The separated channels are then recombined. Such a design provides for user experience in which the entire spectrum from deep blue to infrared (~400-900 nm wavelengths) is in focus.

According to some implementations of the first aspect, a field stop may be provided between the most proximal rod lens and the first beam splitter. The field stop is may be attached to the beam splitter and prism assembly, or may be an integral part of the beam splitter and prism assembly. The field stop may be printed on a glass component and cemented to the beam splitter and prism assembly.

According to some implementations of the first aspect, the beamsplitter and prism assembly is optically positioned at an internal telecentric image space. Such arrangement may include a field stop optically positioned at an internal image in the internal telecentric image space.

According to a second aspect of the invention, endoscopic imaging system is provided including an endoscopic device with a shaft and one or more rod lenses arranged along the shaft to pass image light from a distal end to a proximal end of the shaft. A beam splitter and prism assembly are optically positioned proximal to a most proximal of the one or more rod lenses, with a first beamsplitter that directs a first portion of light with a first spectral content along a first optical path and a second portion of light with a second spectral content, different from the first, along a second optical path. A second beamsplitter is adapted to recombine the first portion of light and the second portion of light to a common optical axis. The first optical path and the second optical path compensate for the chromatic aberration of the endoscope lenses such that the first portion of light and the second portion of light can be focused onto substantially the same image plane. The first portion of light contains both visible and infrared spectral content.

According to some implementations of the second aspect, the second portion of light contains both visible and infrared spectral content. The visible content of the second portion of light may be of longer wavelength than the visible content of the first portion of light, with the infrared content of the second portion of light being of shorter wavelength than the infrared portion of the first portion of light. In such case, the first portion of light may include light with wavelengths less than approximately 450 nm and longer than approximately 750 nm, and the second portion of light may include light with wavelengths between approximately 450 nm and 750 nm.

According to a third aspect of the invention, an optical device for use in endoscope procedures is provided, the device operable with white light and fluoresced light outside the visible band. The device has an elongated shaft having multiple lenses including an objective lens group forming an image at the distal end and multiple rod lenses which relay the image formed at the distal end to the proximal end. A chromatic adjustment assembly is optically positioned at an internal telecentric image space proximal to the most proximal rod lens, and includes (i) a first beamsplitter adapted to direct a first portion of light with a first spectral content along a first optical path and a second portion of light with a second spectral content, different from the first, along a second optical path, and (ii) a second beamsplitter optically arranged proximal to the first beamsplitter and adapted to recombine the first portion of light and the second portion of light to a common optical axis. The first optical path and the second optical path are adapted to compensate for chromatic aberration of the endoscope multiple lenses such that the first portion of light and the second portion of light are focused onto substantially the same image plane.

In some implementations of the third aspect, the chromatic adjustment assembly further includes at least two prisms having different indices of refraction and positioned in the first and second optical paths, respectively.

In some implementations of the third aspect, the beamsplitter and prism assembly has an associated field stop optically positioned at an internal image in the internal telecentric image space.

According to some implementations of the first aspect, the visible content of the second portion of light is of longer wavelength than the visible content of the first portion of light, and the infrared content of the second portion of light is of shorter wavelength than the infrared portion of the first portion of light. In such case, the first portion of light may include light with wavelengths less than approximately 450 nm and longer than approximately 750 nm, and the second portion of light may include light with wavelengths between approximately 450 nm and 750 nm.

These and other features of the invention will be apparent from the following description of the preferred embodiments, considered along with the accompanying drawings.

BRIEF DESCRIPTION OF THE DRAWINGS

The present invention will become more fully understood from the detailed description given herein and the accompanying drawings which are given by way of illustration only, and thus are not limitative of the present invention, and wherein.

DETAILED DESCRIPTION OF EXAMPLE EMBODIMENTS

As used herein, first elements (e.g., sensors and lenses) that are "optically arranged" in relation to other elements, refers to the first elements' position along a common optical path that includes first and other elements. For example, a lens group optically arranged between an image sensor and an objective, means that the lens group occupies a portion of the optical path that light travels (e.g., from the objective to the image sensor) for capturing images or video.

Because digital cameras and FI sensors and related circuitry for signal capture and processing are well-known, the present description will be directed in particular to elements forming part of, or cooperating more directly with, a method and apparatus in accordance with the invention. Elements not specifically shown or described herein are selected from those known in the art. Certain aspects of the embodiments to be described are provided in software. Given the system as shown and described according to the invention in the following materials, software not specifically shown, described or suggested herein that is useful for implementation of the invention is conventional and within the ordinary skill in such arts.

Figure 1:
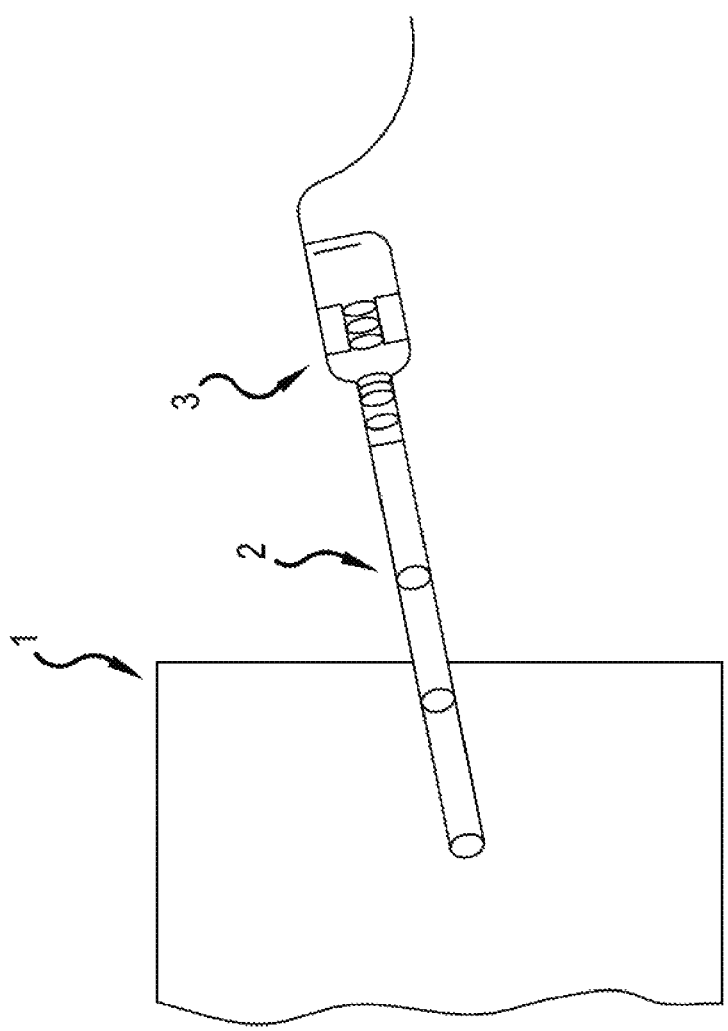
FIG. 1 is diagram of a prior art endoscopic system.
Figure 2:
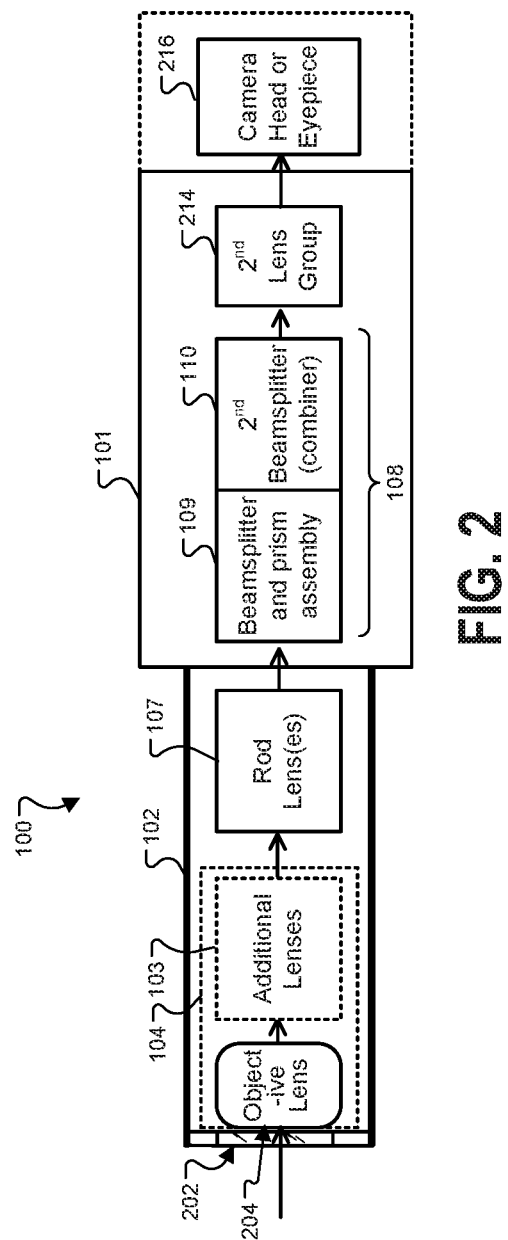
FIG. 2 is a block diagram of an endoscope device according to an example embodiment of the invention.

FIG. 2 is a block diagram of an endoscope device 100 according to an example embodiment of the invention. Endoscope device 100 ("device 100", "endoscope 100") includes a shaft 102 connected to a proximal handle portion 101. Device 100 may instead include an integrated camera or detachable camera head at element 216 with one or more image sensors, or an eyepiece viewer element may be used for scenarios in which fluoresced light outside the visible range is not desired to be viewed directly. Various structural components supporting the depicted elements are omitted in the diagrams herein, as well as other components such as illumination lights sources, fluorescent excitation light sources, and controls, which are known in the art and are not shown in order to avoid obscuring the relevant details of the example embodiments of the invention. At the left is shown the distal tip of the endoscope shaft 102 including a cover glass 202, which in this version faces directly along the longitudinal axis of the shaft 102, but may also be positioned at an angle relative to the longitudinal axis as is known in the art. Behind, or on the proximal side of, the cover glass 202 is shown a preferred position for the objective lens 204, set against or very near cover glass 202 and preferably assembled together with the cover glass in construction. While a wide angle lens is preferred for objective lens 204, this is not limiting and any suitable lens may be used in various embodiments. Objective lens 204 may be part of an objective lens group 104 which may include one or more additional lenses 103. The particular number and arrangement of lenses in the endoscope shaft 102 will vary widely depending on the application. Optically arranged or attached at the proximal side of objective lens 204 or objective lens group 104 is a series of one or more rod lenses 107, which serve to pass the light down shaft 102 in the proximal direction. Rod lenses 107 preferably are adapted to direct the image light to create a telecentric internal image space at the proximal end of the one or more rod lenses, where the chromatic adjustment assembly 108 is positioned as further discussed below. Typically several rod lenses 107 are employed, which may be separated by spacers or other lenses in any suitable manner known in the art. Also, the shaft 102 is typically rigid but shaft design variations are also known to allow rod lenses to be used in a semi-flexible shaft in which flexible joints are present in one or more places along the shaft between the rod lenses, while the shaft is rigid along the portions containing a rod lens. Such a shaft design may be used in various embodiments of the invention.

Optically arranged or attached at the proximal side of the one or more rod lenses 107 is a chromatic adjustment assembly 108, which functions to compensate for chromatic aberration of the endoscope multiple lenses such that a first portion of light and a second portion of light have their chromatic aberration corrected to be focused onto substantially the same image plane. Assembly 108 is positioned within a telecentric internal image space proximal to rod lenses 107. Further, assembly 108 is preferably positioned within the handle portion 101 of device 100, but may partially span the volume of the shaft 102 and handle portion 101. The chromatic adjustment assembly 108 has different forms in different embodiments, but in this version include a beamsplitter and prism assembly 109 wherein a first beamsplitter is adapted to direct a first portion of light with a first spectral content along a first optical path and a second portion of light with a second spectral content, different from the first, along a second optical path. Assembly 108 also includes a second beamsplitter 110 optically positioned at the proximal side of the assembly 109 and configured as a combiner to recombine the first portion of light and the second portion of light to a common optical axis. The first optical path and the second optical path are adapted to compensate for chromatic aberration of the endoscope multiple lenses such that the first portion of light and the second portion of light are focused onto substantially the same image plane. Preferably second beamsplitter 110 is optically coupled to assembly 109 by being cemented with optical cement to faces of elements in assembly 109, as it is in the example embodiments described below.

Optically arranged at the proximal side of the second beamsplitter 110 is a second lens or lens group 214 adapted to receive the light from second beamsplitter 110 and focus the light to an appropriate size for viewing or imaging by the camera, camera head, or eyepiece at element 216. Second lens group 214 typically is a focusing lens group having a total positive power, and is typically the final lens group in the optical path to the sensor or viewing window at element 216. Many suitable lenses and combinations of lenses may be used for second lens group 214. By placing the chromatic adjustment assembly 108 in the telecentric internal image space between the most proximal rod lens and the second lens group 214, longitudinal chromatic aberration can be corrected without affecting lateral chromatic aberration.

Typically, chromatic adjustment assembly 108 is integrated with endoscope device 100 and designed to compensate for the chromatic aberrations inherent in the particular optical path of device 100 including its other lenses. The eyepiece, or the image sensor assembly and its associated electronics (together constituting a camera) may be integrated with the device or may be separate and detachable, such as a detachable eyepiece or a detachable camera head. In various embodiments the invention may therefore constitute an endoscopic device or an imaging system including an endoscopic device 100.

In some versions a system includes an endoscopic device 100 with a shaft 102 and one or more rod lenses 107 arranged along the shaft to pass image light from a distal end to a proximal end of the shaft. A chromatic adjustment assembly 108 includes a beam splitter and prism assembly 109 optically positioned proximal to a most proximal of the one or more rod lenses 107, with a first beamsplitter adapted to direct a first portion of light with a first spectral content along a first optical path and a second portion of light with a second spectral content, different from the first, along a second optical path. The second beamsplitter 110 is adapted to recombine the first portion of light and the second portion of light to a common optical axis. The first optical path and the second optical path compensate for the chromatic aberration of the endoscope lenses such that the first portion of light and the second portion of light can be focused onto substantially the same image plane. In some versions, the first portion of light contains both visible and infrared spectral content. The second portion of light may also contain both visible and infrared spectral content. In such case, the visible content of the second portion of light may be of longer wavelength than the visible content of the first portion of light, and the infrared content of the second portion of light is of shorter wavelength than the infrared portion of the first portion of light. For example, the first portion of light may include light with wavelengths less than approximately 450 nm and longer than approximately 750 nm, and the second portion of light comprises light with wavelengths between approximately 450 nm and 750 nm.

Figure 3:
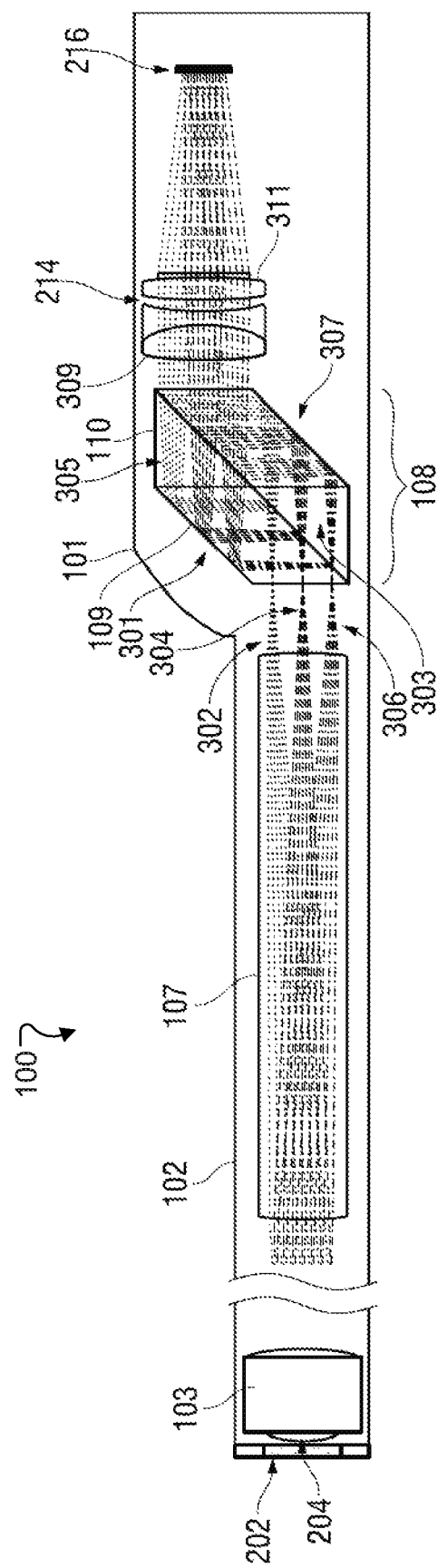
FIG. 3 is a cross section diagram of an endoscope device showing the optical channel construction according to another embodiment.

FIG. 3 is a cross section diagram of an endoscope device 100 showing the optical channel construction according to another embodiment. The depicted optical elements are in diagram form only and are not drawn to scale. The assembly and construction or the endoscope and shaft may vary. As shown, the optical channel includes cover glass 202, covering objective lens 204 which passes the observed image light to an objective lens group 103. The objective lens groups 103 is adapted to direct the light along the channel through one or more rod lenses 107 as discussed above. Lens group 103 may include a prism or prism assembly if the objective lens is at an angle to the shaft longitudinal axis. Next in the optical path after the rod lenses 107 is the chromatic adjustment assembly 108, optically arranged in an internal telecentric image space at the proximal side of the most proximal one of the rod lenses 107, as can be seen by the depicted ray diagram with the distal edge of beamsplitter and prism assembly 109 placed in the image space as can be seen depicted on the drawing where principle ray bundles 302, 304, and 306 converge to form an image space providing an internal telecentric image space for a limited distance. The actual distance from the proximal rod lens 107 to the beamsplitter and prism assembly 109 may vary depending on design, but will typically be from about 1 to 10 mm for a 4-10 mm diameter endoscope shaft. Preferred designs include rod lenses adapted to align the light leaving the most proximal rod lens as closely as possible to parallel to the longitudinal axis of the endoscope shaft (or, if the optical channel is not itself designed to be parallel to the shaft at this area, as closely as possible to parallel to the optical channel center axis). In any event, the rod lenses and any spacer elements may include concave or convex end surfaces to provide positive or negative optical power to achieve the desired internal telecentric image space, or spacer elements between one or more respective rod lens pairs may be implemented as positive or negative power lenses to achieve the same result. Further, while this version shows the chromatic adjustment assembly 108 adjacent to the most proximal rod lens 107, this is not limiting and other lens elements may be included between elements 107 and 108, such as focusing elements or spacer elements.

In this embodiment, beamsplitter and prism assembly 109 includes two prism elements, a parallelogram prism element 301 and a triangular prism element 303, with the edges facing into the page being straight to present faces of the prism along which the light can or reflect as depicted. Beamsplitter and prism assembly 109 helps to provide an image with reduced chromatic aberration compared to conventional endoscopes, and provides better correction in infrared wavelengths (useful for ICG and similar technologies) and in the deep blue than a conventional endoscope. In particular, beam splitter and prism assembly 109 is constructed such that part of the infrared and the deep blue wavelengths can propagate along one optical path while the rest of the visible light and some infrared propagate along a separate path having a different optical path length. The separated channels are then recombined by beamsplitter 110. The advantage provided for the user experience is that the entire spectrum from deep blue to infrared (~400-900 nm wavelengths) is in focus. In addition, chromatic aberration in the deep blue portion of the spectrum is suboptimal in the same direction as the infrared. In typical prior art chromatic aberration solutions, the dispersive properties of the optical materials utilized, and the long glass paths through such materials, make conventional correction of the entire spectrum from deep blue to infrared problematic.

The common path for deep blue wavelengths and part of the infrared wavelengths, with another path for the remainder of the visible and infrared wavelengths, provides a better solution for such a problem. The different paths may be provided in any suitable way. Preferably, the index of refraction for the first path (for example, the path for light wavelengths less than approximately 450 nm and longer than approximately 750 nm) will be lower than that of the second path (for example, carrying light with wavelengths between approximately 450 nm and 750 nm). In this version, beamsplitter and prism assembly 109 includes two prisms, with a dichroic coating on the surface between prisms 301 and 303 allowing a first portion of light to pass through to prism 303, for example, wavelengths less than approximately 450 nm and longer than approximately 750 nm, and reflecting the second portion of light, for example light with wavelengths between approximately 450 nm and 750 nm, back toward the opposing diagonal face of prism 301. In one example version, prisms 301 and 303 have an index of refraction of 1.49, and prisms 305 and 307 have an index of refraction of 1.62.

The opposing face of prism 301 is reflective, reflecting light along the second path in this example toward beamsplitter 110, which is positioned to act as a combiner. Beamsplitter 110 in this version includes a triangular prism 305 and a parallelogram prism 307. The connecting face of prisms 305 and 307 is also coated with a dichroic coating, in this case passing the second portion of light from prism 301, and reflecting the first portion of light (which was reflected off the lower-depicted reflective face of prism 307) along the same path as the second portion. The faces joining elements 109 and 110 are preferably joined by normal optical cement with no dichroic properties, or another suitable joining method passing light straight through. The joining faces of the elements of 109 and 110 may instead be coated with a bandpass coating for the second portion of light (applied between 301 and 305) or a bandstop coating for the second portion of light (between 303 and 307) to improve the isolation between the optical paths and further reduce the power level of any light not travelling along the designated path for its wavelength. Beamsplitter 110 acts to combine the first and second portions of light and align them parallel to the desired optical axis toward second lens group 214. Similar paths may also be provided with different arrangements of prisms for assembly 108, such as six right angle prisms with prisms 301 and 307 each replaced by two right angle prisms having reflective and dichroic surfaces or band-pass/band reflect properties at the surfaces described and passing light straight through the interface of the two right angle prisms.

The second lens group 214 in this version functions as the ocular lens having a total positive optical power focusing the light toward the image sensor at element 216, which in this versions is an integrated camera with an electronic image sensor. Other embodiments may include a focal length for element 214 focusing outside a window at the proximal end of device 100 to an external camera head, or a viewer eyepiece. Lens group 214 includes a doublet achromat lens 309 with a biconcave lens and a bi-convex lens, and a final bi-convex lens 311 which may serve as the eyepiece cover glass or be optically arranged adjacent the eyepiece cover glass. Many other suitable lens arrangements are possible for the second lens group, which, as discussed, may focus the image light toward an internal camera, an external camera head or serve as an eyepiece. In this version the optical axis along the second lens group 214 is offset or deviated from the scope shaft optical axis.

Figure 4:
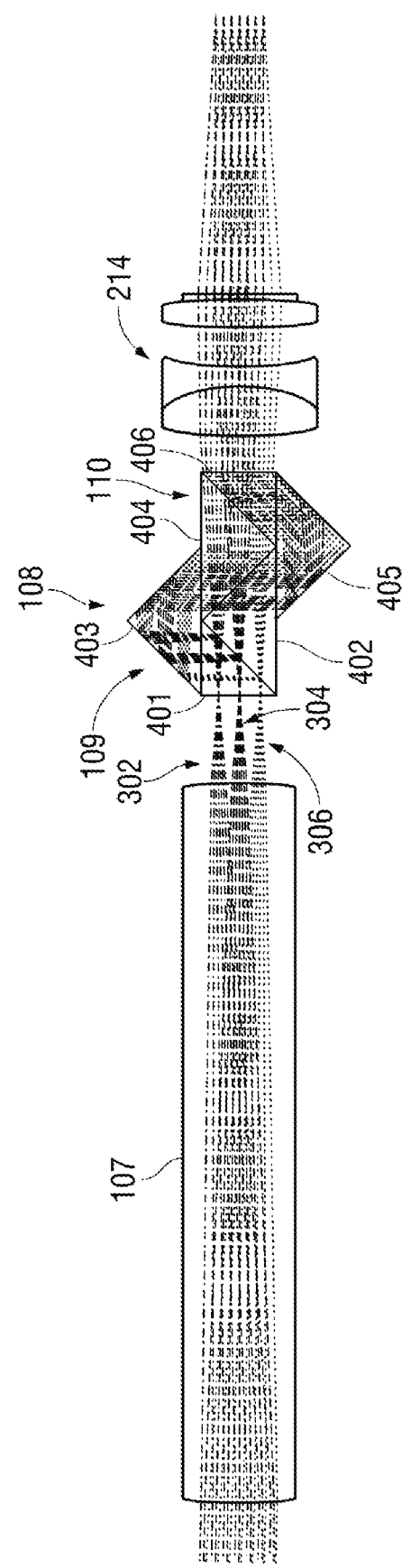
FIG. 4 is a cross section diagram of an endoscope device optical path according to another embodiment, having a more complex chromatic adjustment assembly providing a viewing axis along the shaft optical axis.

FIG. 4 is a cross section diagram of an optical path according to another embodiment, having a more complex chromatic adjustment assembly 108 providing a viewing axis along the shaft 102 optical axis. The objective, camera/eyepiece, and handle housing 101 and shaft 102 are not shown in order to avoid obscuring the invention. The depicted optical path may be employed with endoscope devices and systems having an integrated camera (with one or more image sensors) or an external detachable camera head or eyepiece attachment. In this version, the chromatic adjustment assembly 108 is again optically positioned proximal to the most proximal rod lens. Assembly 108 includes a beamsplitter and prism assembly 109 wherein a first beamsplitter including right angle prism 401 and triangular prism 402 is adapted to direct a first portion of light with a first spectral content along a first optical path to triangular prism 405, and a second portion of light with a second spectral content, different from the first, along a second optical path to triangular prism 403. Assembly 108 also includes a second beamsplitter 110, which includes triangular prism 404 and optical prism 406, optically positioned at the proximal side of the assembly 109 and configured as a combiner to recombine the first portion of light and the second portion of light to a common optical axis. The first optical path and the second optical path are adapted to compensate for chromatic aberration of the endoscope multiple lenses such that the first portion of light and the second portion of light are focused onto substantially the same image plane.

The depicted ray diagrams show reflections in the two optical paths. The first optical path through prisms 402 and 405 includes a bandpass coating at the interface of 401 and 402 for the first portion of light, a reflective surface at the interface of prisms 402 and 404, and a reflective surface on both the lower walls of prism 405. Beamsplitter 110 then includes a coating at the interface of prisms 406 and 404 to reflect the first portion of light toward second lens group 214, and pass the second portion of light from prism 404. The second path for the second portion of light reflects as depicted from the coating at the interface of prisms 401 and 402, upward to prism 403 and is similarly reflected to beamsplitter 110 (configured as a combiner) and reflected off of the left wall of prism 404, then passed through the interface of prisms 404 and 406. As described above, the particular path that the different portions of light follow may be switched, but the prism media on each side of the beam-splitter interfaces (the interface of 401 and 402, and the interface of 404 and 406) have the same index of refraction.

Figure 5:
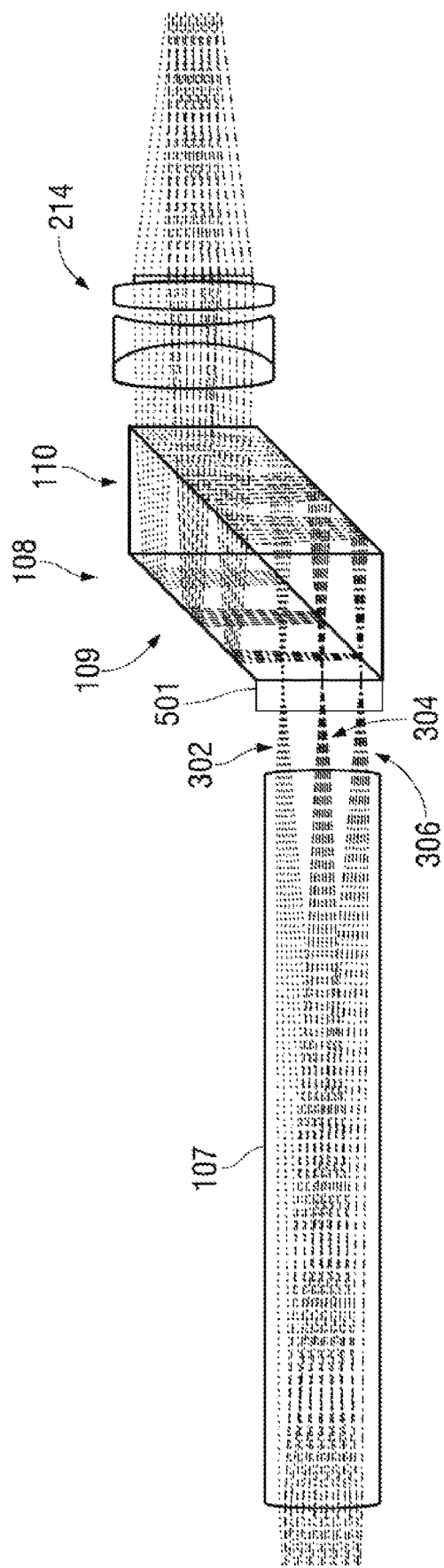
FIGS. 5-6 are cross section diagrams optical paths for example embodiments including field stops.
Figure 6:
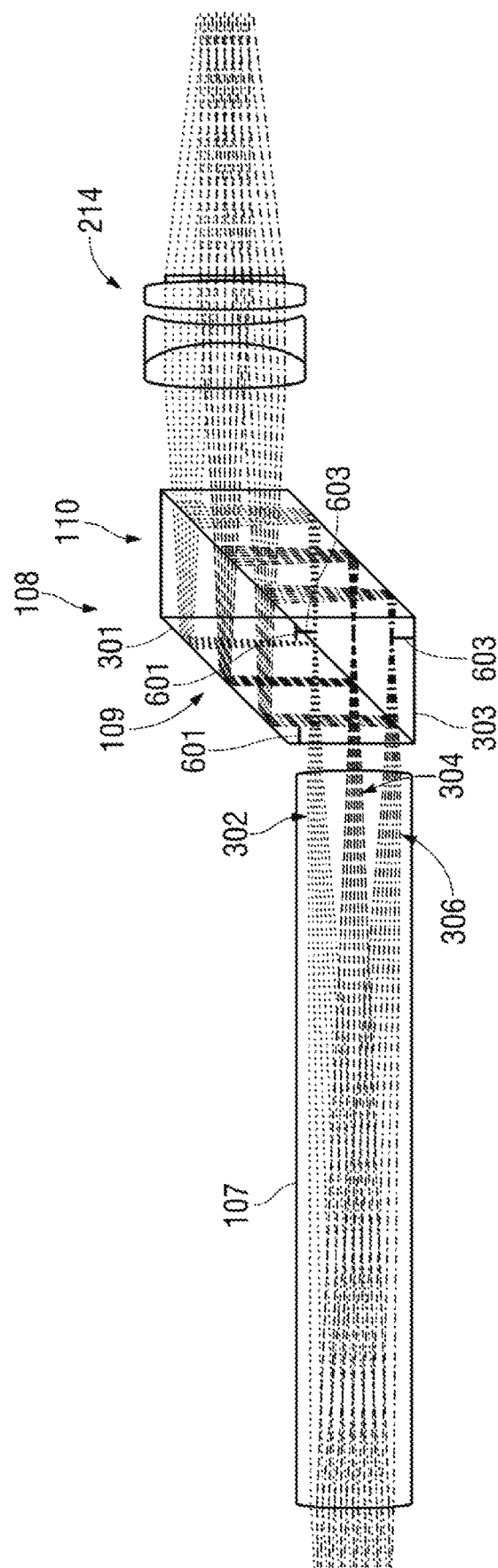

FIGS. 5-6 are cross section diagrams optical paths for example embodiments including field stops. In FIG. 5, the optical channel is similar in construction to that of FIG. 3, with the addition of a flat glass element 501 is provided attached, preferably with optical cement, to the distal face of chromatic adjustment assembly 108. A field stop is printed on flat glass element 501, preferably on its proximal face. Other versions may simply provide a field stop positioned between the most proximal rod lens 107 and the first beam splitter of the beam splitter and prism assembly 109, or may provide a field stop attached to the beam splitter and prism assembly 109 in another manner. The field stops are preferably placed at the internal image, as indicated by the most convergent part of the depicted ray diagrams. The field stop prevents light from outside the designed field of view, where optical performance is not optimized, from propagating through the optical system. In some embodiments it allows the chromatic adjustment assembly 108 to be placed closer to the most proximal rod lens 107 while still performing its function, providing a smaller overall optical path. The same function may be achieved, as depicted in FIG. 6, by constructing the field stop as an integral part of the beam splitter and prism assembly. FIG. 6 is a cross section diagram of an optical path according to another embodiment, in which the chromatic adjustment assembly 108 includes an integrated field stop. As shown, chromatic adjustment assembly 108 is placed closer to the most proximal rod lens 107 than the arrangement of FIG. 3, allowing the chromatic adjustment assembly to better fit in the limited space available in scope designs. Field stops 601 are positioned inside prism 301 to provide a field stop for the second path of light reflecting through the upward depicted trajectory. Field stops 603 are placed inside prism 301, providing a field stop for the first path of light reflecting through the lower trajectory. The depicted field stops 601 and 603 span the entire optical path in the Z dimension (into the page), and may be constructed by milling or cutting slots into the individual prisms 301 and 303 before assembling the chromatic adjustment assembly 108, and inserting a suitable opaque material into the slots.

Figure 7:
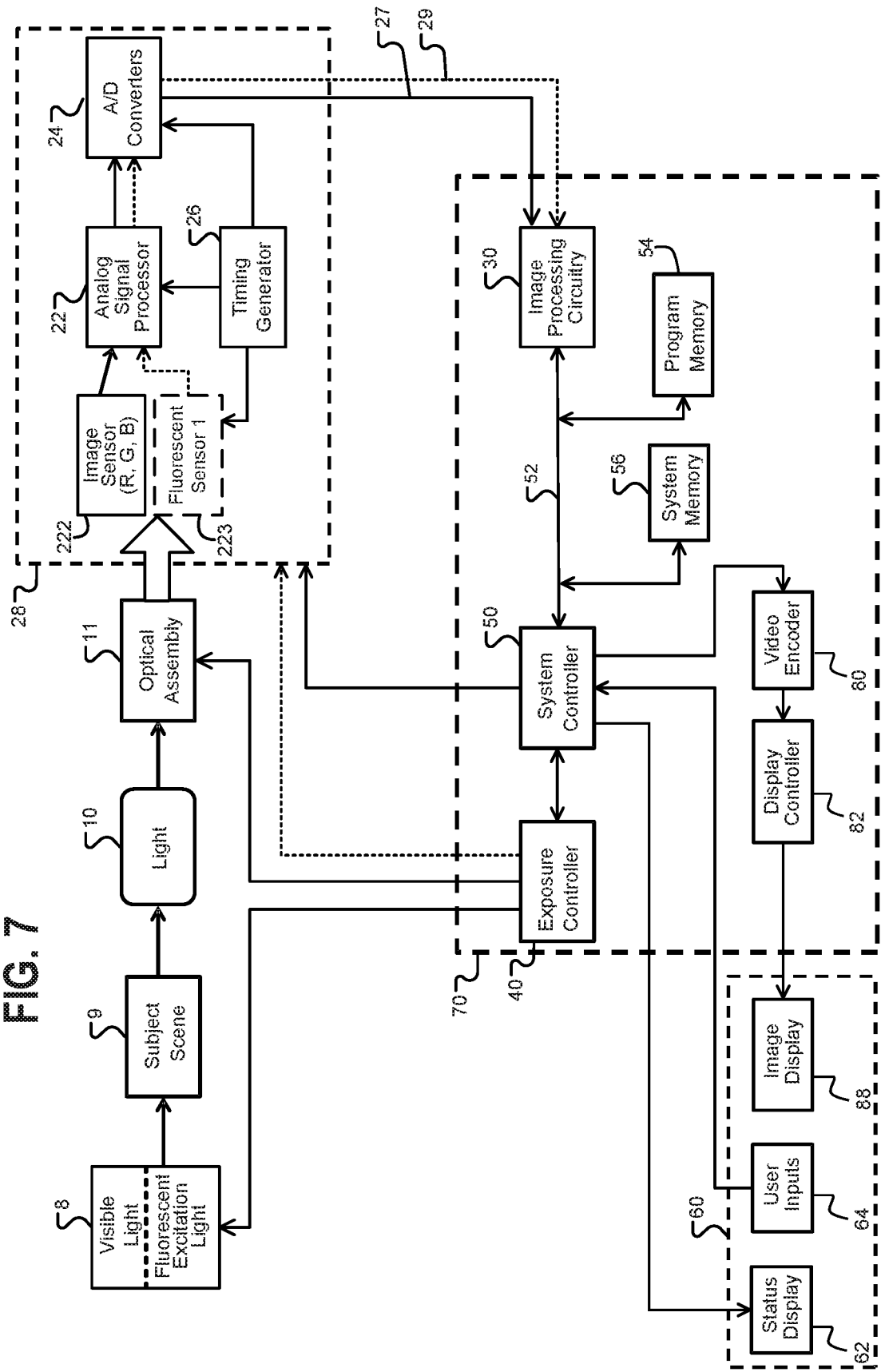
FIG. 7 is a hardware block diagram of system including an example image capture device according to an example embodiment of the invention.

Referring to FIG. 7, a block diagram of system including an image capture device and an endoscope device having an improved optical path as described above. The invention is applicable to more than one type of device enabled for image capture, such as FI-capable endoscopes, other FI medical imaging devices. The preferred version is an imaging scope system, such as an endoscope.

As shown in the diagram of an endoscope device system, a light source 8 illuminates subject scene 9 with visible light and/or fluorescent excitation light, which may be outside the visible spectrum in the ultra-violet range or the infra-red/near infrared range, or both. Light source 8 may include a single light emitting element configured to provide light throughout the desired spectrum, or a visible light emitting element and a one or more fluorescent excitation light emitting elements. Further, light source 8 may include fiber optics passing through the body of the scope, or other light emitting arrangements such as LEDs or laser diodes positioned at or near the front of the scope.

As shown in the drawing, light 10 reflected from (or, alternatively, as in the case of fluorescence, excitation light 8 absorbed and subsequently emitted by) the subject scene is input to an optical assembly 11, where the light is focused to form an image at a solid-state image sensor(s) 222 and/or fluoresced light sensor(s) 223.

Optical assembly 11 includes at least one lens, which may be a wide-angle lens element such that optical assembly 11 focuses light which represents a wide field of view. The various embodiments and variations of the chromatic adjustment assembly 108 may be positioned as described above as part of the optical assembly. As discussed above, portions of the optical assembly may be embodied in a camera head or other first optical device, while other portions are in an endoscope or other scope device, or the optical assembly 11 may contained in a single imaging device. Image sensor 222 (which may include separate R, G, and B sensor arrays) and fluoresced light sensor 223 convert the incident visible and invisible light to an electrical signal by integrating charge for each picture element (pixel). It is noted that fluoresced light sensor 223 is shown as an optional dotted box because embodiments may use the RGB image sensor 222 to detect only white light images or to also detect fluoresced light (e.g., NIR, ICG, FI). The latter scheme may be used when the fluoresced light is in a spectrum detectable by image sensor 222 that is in or near the visible light spectrum typically detected by a RGB sensor arrays.

The image sensor 222 and fluoresced light sensor 223 may be active pixel complementary metal oxide semiconductor sensor (CMOS APS) or a charge-coupled device (CCD).

The total amount of light 10 reaching the image sensor 222 and/or fluoresced light sensor 223 is regulated by the light source 8 intensity, the optical assembly 11 aperture, and the time for which the image sensor 222 and fluoresced light sensor 223 integrates charge. An exposure controller 40 responds to the amount of light available in the scene given the intensity and spatial distribution of digitized signals corresponding to the intensity and spatial distribution of the light focused on image sensor 222 and fluoresced light sensor 223.

Exposure controller 40 also controls the emission of fluorescent excitation light from light source 8, and may control the visible and fluorescent light emitting elements to be on at the same time, or to alternate to allow fluoresced light frames to be captured in the absence of visible light if such is required by the fluorescent imaging scheme employed. Exposure controller 40 may also control the optical assembly 11 aperture, and indirectly, the time for which the image sensor 222 and fluoresced light sensor 223 integrate charge. The control connection from exposure controller 40 to timing generator 26 is shown as a dotted line because the control is typically indirect.

Typically exposure controller 40 has a different timing and exposure scheme for each of sensors 222 and 223. Due to the different types of sensed data, the exposure controller 40 may control the integration time of the sensors 222 and 223 by integrating sensor 222 up to the maximum allowed within a fixed 60 Hz or 50 Hz frame rate (standard frame rates for USA versus European video, respectively), while the fluoresced light sensor 223 may be controlled to vary its integration time from a small fraction of sensor 222 frame time to many multiples of sensor 222 frame time. The frame rate of sensor 222 will typically govern the synchronization process such that images frames based on sensor 223 are repeated or interpolated to synchronize in time with the 50 or 60 fps rate of sensor 222.

Analog signals from the image sensor 222 and fluoresced light sensor 223 are processed by analog signal processor 22 and applied to analog-to-digital (A/D) converter 24 for digitizing the analog sensor signals. The digitized signals each representing streams of images or image representations based on the data, are fed to image processor 30 as image signal 27, and first fluorescent light signal 29. For versions in which the image sensor 222 also functions to detect the fluoresced light, fluoresced light data is included in the image signal 27, typically in one or more of the three color channels.

Image processing circuitry 30 includes circuitry performing digital image processing functions to process and filter the received images as is known in the art. Image processing circuitry may include separate, parallel pipelines for processing the visible light image data and the FI image data separately. Such circuitry is known in the art and will not be further described here.

Image processing circuitry 30 may provide algorithms, known in the art, for combining visible light imagery with FI imagery in a combined image display, and further highlighting or emphasizing the FI imagery for easily distinguishing the presence of fluorescing features in the image.

Timing generator 26 produces various clocking signals to select rows and pixels and synchronizes the operation of image sensor 222 and fluorescent sensor 223, analog signal processor 22, and A/D converter 24. Image sensor assembly 28 includes the image sensor 222 and fluorescent sensor 223, adjustment control 20, the analog signal processor 22, the A/D converter 24, and the timing generator 26. The functional elements of the image sensor assembly 28 can be fabricated as a single integrated circuit as is commonly done with CMOS image sensors or they can be separately-fabricated integrated circuits.

The system controller 50 controls the overall operation of the image capture device based on a software program stored in program memory 54. This memory can also be used to store user setting selections and other data to be preserved when the camera is turned off.

System controller 50 controls the sequence of data capture by directing exposure controller 40 to set the light source 8 intensity, the optical assembly 11 aperture, and controlling various filters in optical assembly 11 and timing that may be necessary to obtain image streams based on the visible light and fluoresced light. In some versions, optical assembly 11 includes an optical filter configured to attenuate excitation light and transmit the fluoresced light. A data bus 52 includes a pathway for address, data, and control signals.

Processed image data are continuously sent to video encoder 80 to produce a video signal. This signal is processed by display controller 82 and presented on image display 88. This display is typically a liquid crystal display backlit with light-emitting diodes (LED LCD), although other types of displays are used as well. The processed image data can also be stored in system memory 56 or other internal or external memory device.

The user interface 60, including all or any combination of image display 88, user inputs 64, and status display 62, is controlled by a combination of software programs executed on system controller 50. User inputs typically include some combination of typing keyboards, computer pointing devices, buttons, rocker switches, joysticks, rotary dials, or touch screens. The system controller 50 manages the graphical user interface (GUI) presented on one or more of the displays (e.g. on image display 88). In particular, the system controller 50 will typically have a mode toggle user input (typically through a button on the endoscope or camera head itself, but possibly through a GUI interface), and in response transmit commands to adjust image processing circuitry 30 based on predetermined setting stored in system memory. Preferably a system employed with any of the device designs herein provides ability to toggle between at least two modes, visible light and FI modes, and more preferably a combined mode is included in which FI images are combined or overlaid with visible images in a suitable manner known in the art. Such settings may include different settings for different models of scopes that may be attached to a camera head or other imaging device containing image sensor assembly 28.

Image processing circuitry 30 is one of three programmable logic devices, processors, or controllers in this embodiment, in addition to a system controller 50 and the exposure controller 40. Image processing circuitry 30, controller 50, exposure controller 40, system and program memories 56 and 54, video encoder 80 and display controller 82 may be housed within camera control module (CCM) 70.

CCM 70 may be responsible for powering and controlling light source 8, image sensor assembly 28, and/or optical assembly 11. In some versions, a separate front end camera module may perform some of the image processing functions of image processing circuitry 30.

Although this distribution of imaging device functional control among multiple programmable logic devices, processors, and controllers is typical, these programmable logic devices, processors, or controllers can be combinable in various ways without affecting the functional operation of the imaging device and the application of the invention. These programmable logic devices, processors, or controllers can comprise one or more programmable logic devices, digital signal processor devices, microcontrollers, or other digital logic circuits. Although a combination of such programmable logic devices, processors, or controllers has been described, it should be apparent that one programmable logic device, digital signal processor, microcontroller, or other digital logic circuit can be designated to perform all of the needed functions. All of these variations can perform the same function and fall within the scope of this invention.

As used herein the terms "comprising," "including," "carrying," "having" "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The foregoing has outlined rather broadly the features and technical advantages of the invention in order that the detailed description of the invention that follows may be better understood. It should be appreciated by those skilled in the art that the conception and specific embodiments disclosed may be readily utilized as a basis for modifying or designing other structures for carrying out the same purposes of the invention. It should also be realized by those skilled in the art that such equivalent constructions do not depart from the scope of the invention as set forth in the appended claims.

Although the invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

The invention claimed is:

1. An endoscopic imaging system comprising:
an endoscopic device including a shaft and one or more rod lenses arranged along the shaft to pass image light from a distal end to a proximal end of the shaft;
a beam splitter and prism assembly optically positioned proximal to a most proximal of the one or more rod lenses, wherein a first beamsplitter directs a first portion of light with a first spectral content along a first optical path and a second portion of light with a second spectral content, different from the first, along a second optical path;
a second beamsplitter to recombine the first portion of light and the second portion of light to a common optical axis;
wherein the first optical path and the second optical path compensate for a chromatic aberration of the endoscope lenses such that the first portion of light and the second portion of light can be focused onto substantially the same image plane;
wherein the first portion of light contains both visible and infrared spectral content;
wherein the second portion of light contains both visible and infrared spectral content; and
wherein the visible content of the second portion of light is of longer wavelength than the visible content of the first portion of light, and the infrared content of the second portion of light is of shorter wavelength than the infrared portion of the first portion of light.

2. The system of claim 1 wherein the first portion of light comprises light with wavelengths less than approximately 450 nm and longer than approximately 750 nm, and the second portion of light comprises light with wavelengths between approximately 450 nm and 750 nm.

3. The system of claim 1 wherein the visible spectral content of the first portion of light is discontinuous with the infrared spectral content of the first portion of light.

4. The system of claim 1 wherein the rod lenses are adapted to direct an image light to create an internal telecentric image space at the proximal end of the one or more rod lenses, and wherein the beam splitter and prism assembly is optically positioned at the internal telecentric image space.

5. The system of claim 1 wherein said beam splitter and prism assembly comprises at least one bandstop coating positioned along at least one of the first optical path or the second optical path, the bandstop coating improving the isolation between the optical paths and reducing the power level of any light not travelling along the designated path for its wavelength.

6. The system of claim 1 wherein said beam splitter and prism assembly comprises at least one bandpass coating positioned along at least one of the first optical path or the second optical path, the bandpass coating improving the isolation between the optical paths and reducing the power level of any light not travelling along the designated path for its wavelength.

* * * * *